(12) United States Patent
Wood

(10) Patent No.: US 12,115,315 B2
(45) Date of Patent: Oct. 15, 2024

(54) SLEEP APNEA NASAL PILLOWS DEVICE

(71) Applicant: REMSleep Holdings Inc, Tampa, FL (US)

(72) Inventor: Thomas Jackson Wood, Waycross, GA (US)

(*) Notice: Subject to any disclaimer, the term of this patent is extended or adjusted under 35 U.S.C. 154(b) by 849 days.

(21) Appl. No.: 17/215,589

(22) Filed: Mar. 29, 2021

(65) Prior Publication Data

US 2021/0213229 A1 Jul. 15, 2021

Related U.S. Application Data

(63) Continuation-in-part of application No. 15/595,990, filed on May 16, 2017, now Pat. No. 10,987,481.

(60) Provisional application No. 62/355,493, filed on Jun. 28, 2016.

(51) Int. Cl.
*A61M 16/06* (2006.01)

(52) U.S. Cl.
CPC .... *A61M 16/0666* (2013.01); *A61M 16/0622* (2014.02)

(58) Field of Classification Search
CPC .......... A61M 16/0683; A61M 16/0666; A61M 16/0611
See application file for complete search history.

(56) References Cited

U.S. PATENT DOCUMENTS

| | | | |
|---|---|---|---|
| 3,145,711 A | 8/1964 | Beber | |
| 4,782,832 A | 11/1988 | Trimble | |
| 5,533,506 A | 7/1996 | Wood | |
| 6,478,026 B1 | 11/2002 | Wood | |
| 6,595,215 B2 | 7/2003 | Wood | |
| 6,776,162 B2 | 8/2004 | Wood | |
| 6,807,967 B2 | 10/2004 | Wood | |
| 6,863,069 B2 | 3/2005 | Wood | |

(Continued)

FOREIGN PATENT DOCUMENTS

| | | |
|---|---|---|
| EM | 000683396-0001 | 5/2007 |
| IN | 237892-0001 | 6/2012 |
| JP | D1430470 | 12/2011 |

OTHER PUBLICATIONS

ResMed Nasal Pillow. Jun. 6, 2017. Site visited Dec. 3, 2022. [https://www.amazon.com/ResMed-AirFit-Nasai-Pillows-Cushions/dp/B01NOSXUC4/ref=sr_1_2?keywords=sleep+apnea+nasal+pillow&qid=1670122899&sprefix=sleep+apnea+nasal%2Caps%2C152&sr=8-2] (Year: 2017).

(Continued)

*Primary Examiner* — Margaret M Luarca
(74) *Attorney, Agent, or Firm* — Larson & Larson; Frank Liebenow; Justin P. Miller

(57) ABSTRACT

An integrated cannula with interface pillows includes a cannula section having a gas inlet for receiving gas, exhalation holes for venting exhalation gas to the atmosphere, and nubs for attaching a head strap. There are two interface pillows formed from a pliable material extend from the cannula section. Each of the interface pillows having an insertion tip that is distal from where each of the interface pillows meets the cannula section. An insertion bulge extends from each interface pillow between the insertion tip and the cannula section, limiting an insertion distance of the insertion tip. An insertion area of each interface pillow extends between the insertion bulge and the insertion tip during use, the insertion bulge is configured to seal against an outer edge of the nostril of a nose.

15 Claims, 9 Drawing Sheets

(56) References Cited

U.S. PATENT DOCUMENTS

| | | |
|---|---|---|
| 6,997,177 B2 | 2/2006 | Wood |
| 6,997,187 B2 | 2/2006 | Wood et al. |
| 7,000,613 B2 | 2/2006 | Wood et al. |
| 7,059,328 B2 | 6/2006 | Wood |
| 6,994,089 B2 | 7/2006 | Wood |
| D533,269 S | 12/2006 | McAuley |
| 7,188,624 B2 | 3/2007 | Wood |
| 7,191,781 B2 | 3/2007 | Wood |
| D551,340 S | 9/2007 | Wood et al. |
| D583,049 S | 12/2008 | Chandran |
| 7,472,707 B2 | 1/2009 | Wood et al. |
| D589,139 S | 3/2009 | Guney |
| D589,140 S | 3/2009 | Guney |
| D612,933 S | 3/2010 | Prentice |
| D612,934 S | 3/2010 | Prentice |
| D618,336 S | 6/2010 | Wood |
| D627,059 S | 11/2010 | Wood et al. |
| D639,418 S | 6/2011 | Prentice |
| D645,557 S | 9/2011 | Scheiner |
| RE42,843 E | 10/2011 | Srickland et al. |
| D661,796 S | 6/2012 | Andrews |
| D664,639 S | 7/2012 | Hoke |
| D674,480 S | 1/2013 | Prentice |
| D687,539 S | 8/2013 | Matula, Jr. |
| 9,138,553 B2 | 9/2015 | Wood |
| D746,468 S | 12/2015 | Meadows |
| 9,901,700 B2 | 2/2018 | McAuley et al. |
| 9,919,121 B2 | 3/2018 | Wood |
| D863,540 S | 10/2019 | Collazo |
| D868,239 S | 11/2019 | Collazo |
| D868,240 S | 11/2019 | Collazo |
| D878,545 S | 3/2020 | Scheiner |
| 10,987,481 B2 | 4/2021 | Wood |
| 2004/0226566 A1 | 11/2004 | Gunaratnum et al. |
| 2005/0028821 A1 | 2/2005 | Wood |
| 2005/0235999 A1 | 10/2005 | Wood |
| 2006/0283461 A1 | 12/2006 | Lubke et al. |
| 2012/0204870 A1* | 8/2012 | McAuley et al. A61M 16/0666 |
| 2016/0015921 A1 | 1/2016 | Harrison et al. |
| 2017/0143926 A1 | 5/2017 | Allum |
| 2017/0368285 A1 | 12/2017 | Wood |
| 2018/0078725 A1 | 3/2018 | Richardson et al. |
| 2021/0213229 A1 | 7/2021 | Wood |
| 2023/0149653 A1 | 5/2023 | Wood |

OTHER PUBLICATIONS

Swift FX Pillow—Small by ResMed. Sep. 5, 2011. Site visited Dec. 3, 2022. [https://www.amazon.com/Swift-FX-Nasai-Pillow-Small/dp/B005LAPE0K!ref=sr1_69?keywords=sleep+apnea+nasal+pillow&qid=1670123402&sprefix=sleep+apnea+nasal%2Caps%2C152&sr=8-69] (Year: 2011).

Philips Respironics. Sep. 19, 2018. Site visited Dec. 3, 2022. [https://www.amazon.com/ Philips-Respironics-Nuance-Replacement-Pillows/dp/B07DGFH9MD/ref=sr_1_4?crid=2YHXIHO3Y7Q2E&keywords=nasal+pillow&qid=1670123733&sprefix=nasal+pillow%2Caps%2C85&sr=8-4] (Year: 2018).

Nose Pillow with Headgear. Nov. 11, 2022. Site visited Sep. 28, 2023. [https://www.amazon.com/Nose-Pillow-Headgear-P10-Replacement/dp/B0BM435Y2M/ref=sr_1_6?crid=1U7MROB4IUCUU&keywords=Sleep%2BApnea%2BCannula%2Band%2BNasal%2BPillows%2BDevice&qid=1695953707&s=industrial&sprefix=sleep%2Bapnea%2Bcannula%2Band%2Bnasal%2Bpillows%2Bdevice%2Cindustrial%2C158&sr=1-6&th=1] (Year: 2022).

ResMed Nasal Pillow. Jun. 6, 2017. Site visited Sep. 28, 2023. [https://www.amazon.com/ResMed-AirFit-Nasal-Pillows-Cushions/dp/B01NOSXUC4/ref=asc_df_B01N0SXUC4/?tag=hyprod-20&linkCode=df0&hvadid=507695844407&hvpos=&hvnetw=g&hvrand=9683724060980129548&hvpone=&hvptwo=&hvqmt=&hvdev=c&hvdvcmdl=&hvlocint=&hvlocphy=9008141&hvtargid=pla-12759293231 14&psc=1] (Year: 2017).

* cited by examiner

SLEEP APNEA NASAL PILLOWS DEVICE

CROSS-REFERENCE TO RELATED APPLICATION

This application is a continuation-in-part of U.S. patent application Ser. No. 15/595,990 filed May 16, 2017 which claims the benefit of U.S. provisional application No. 62/355,493 filed on Jun. 28, 2016, the disclosure of which are incorporated by reference.

FIELD

This invention relates to the field of medicine and more particularly to a nasal interface for the delivery of gases in the treatment of sleep apnea and other respiratory problems.

BACKGROUND

Ventilation is commonly used in the treatment of respiratory conditions such as sleep apnea. On such form of ventilation is a continuous positive air pressure system often referred to as a CPAP system. Continuous positive air pressure systems typically include a mask that interfaces to a user's mouth or nasal passages, supplying air pressure from an air flow generator that is typically located in the proximity of the user. The mask directs the flow of air into the breathing passage of the user while allowing the user to exhale.

For the treatment of sleep apnea, the continuous positive air pressure system is worn while the user sleeps. In continuous positive air pressure system in which the mask interfaces with the user's nostrils, the nostril interface need be held in place and maintain a seal so that, as the user moves during sleep, the mask/nostril interface remains intact and sealed to provide positive airway pressure.

The mask/nostril interface is often referred to as pillow interfaces. An end of the pillow interfaces is inserted partially into each nostril, maintaining an air-tight seal. As the pillow interfaces are worn while the user sleeps, it is important that the pillow interfaces be as comfortable as possible. If the seal is not air-tight, less positive airway pressure is delivered and, the break in the seal will often create noise that may impact the user's sleep. Further, and the pillow is inserted into the nostril, deformation of the pillow reduces airflow and increases turbulence leading to further lowering airflow and creating additional noise.

Another issue with continuous positive air pressure system is the flow velocity of the positive airway pressure. In providing an adequate volume of air for each breath the patient takes (inhalation), the continuous positive air pressure system must provide a minimum volume per time period. Tradeoffs are made between providing greater volumes by using larger orifices or by using smaller orifices and increasing the velocity of the provided air. Unfortunately, when the velocity of the provided air is increased, several user issues occur including burning sensations in the user's sinuses, drying of the user's sinuses, a compromised therapeutic index, and increased noise that is undesirable when the user is trying to sleep.

Existing continuous positive air pressure systems have pillow interfaces that are generally round in cross-sectional area whereas the human nostril is not. These pillow interfaces cause discomfort when worn as the nasal septum is typically more sensitive to pressure and is typically relatively flat in areas of the nasal openings, in particular, the septum. Round cross-sectional shapes do not interface well with flat walls and, as an accommodation, prior pillow interfaces are typically made of a soft material that deforms and flattens when inserted. This flattening reduces the cross-sectional area of these prior nasal pillows, resulting in an acceleration of the air velocity, and therefore, the issues cited above.

The interface pillows of prior continuous positive air pressure systems have numerous issues, some of which are:
 a. Pressure drop within the closed system/cannula.
 b. Lack of ability to deliver an adequate volume of inspired air to the patient.
 c. Air velocity delivered through these pillow interfaces is often high, leading to burning sensations, drying of sinuses, etc.
 d. Such pillows leak if required to deliver more than 10 centimeters of water pressure. Such leaks cause noise disturbances.
 e. Such pillow interfaces lead to discomfort at the bottom of the nostrils.
 f. Head gear often needs to be adjusted too tight for patient comfort.
 g. Air leaks often occur from slight movement of the head.
 h. Lower levels of air deliver often lead to a decrease in blood oxygen saturation during sleep.
 i. These interfaces pillows fit within the nostrils in a way that leads to a disproportionate amount of pressure being applied against the septum (center cartilage) of the nostrils, causing discomfort. The septum is the most sensitive area of the nostrils.

Many of the above issues relate to the shape of the prior-art interface pillows, the material of which they are made, and the resiliency of the materials. As the shape of the prior-art interface pillows is not optimal for sealing within the nostrils of a user, to compensate for such, the prior-art interface pillows are made of very soft material that is easily deformed under pressure. The prior-art interface pillows, after insertion, deform to seal as best that then can within the nostrils of the user. This deformation provides pressure on the sensitive septum of the user's nose, causing discomfort. This deformation also reduces the cross-sectional area of the air passage of each prior-art interface pillow, causing an increase in air flow velocity and noise. The increase in air flow velocity leads to dryness, a sudden burning sensation in the nostrils, and stuffiness in the sinuses. Higher air flow velocity and lower volume of incoming air is less efficient at correcting apnea and often interrupts normal breathing patterns.

Further, most prior interface pillow designs included turning points for the incoming air, some as much as 90 degrees, resulting in turbulence, pressure drop, and a decrease in the therapeutic index of the treatment. As a result of this, more pressure is typically required to deliver the required increased flow rate which partially compensates for inadequate air volume needed for treatment. This increase in air velocity increases unwanted side effects. An increase in air flow velocity is not preferred over supplying adequate air volume.

It should also be noted that with each incremental increase in driving pressure beyond 7 centimeters of water pressure, there is less and less proportionate therapeutic effect. Increases in driving pressure beyond 9 to 10 centimeters of water has little, if any, therapeutic effect using a prior-art interface pillows, and likely only exacerbate the negative effects. Most prior interface pillows will not hold pressures of more than 9 to 10 centimeters of water pressure. This has been one of the significant limitations of such pillow interfaces and only patients with mild obstructive sleep apnea typically have success with the prior interface pillows due to this limitation.

The prior interface pillows create a seal by applying pressure to the inner rim of the nose. The seal is tenuous. Head movement often causes a significant and annoying air leak unless the head gear is noticeably too tight. The apex of the prior interface pillows (where the air flow passes into the nostrils) is very non-structural and the inner diameter of the prior interface pillows is easily compromised when pushed into the nostrils. This often decreases the cross-sectional flow space and air volume delivered, which in turn, further increases the velocity and/or pressure drop of the air flow entering into the nostrils. The area directly beneath the prior interface pillows where they fit against the nostrils becomes narrowed or compromised when encountering pressure against the bottom of the nose created by the head gear. This creates another source of restriction to air flow resulting in a decrease in delivered air volume, pressure drops, an increase of incoming air velocity, and a reduced positive effect.

Based on typical adult inspiratory demand; a patient's respiratory rate, in many cases, will decrease using the prior interface pillows because less air volume is available, which will take longer to complete the inspiratory cycle. The respiratory rate has been seen to decrease from a normal 12 to 14 breaths per minute down to 9 breaths per minute. This interruption of normal respiratory rate often creates a feeling of suffocation and reduced compliance (usage) of the system.

If the inspiratory cycle is prolonged, the expiratory cycle is also prolonged and the lungs may not empty completely before the inspiratory cycle is initiated. An increase in driving pressure will likely be required, but the increase in driving pressure only partially compensates for the inadequate volume of air that must be delivered to maintain an adequate tidal volume and minute ventilation that feels normal to the user. The result is that the user's normal breathing patterns are disrupted, the user feels insecure, a feeling of suffocation and impending doom for some, and less likely to achieve restful sleep. The inadequate lower inspired air volume also creates the need to provide a lower cross-sectional flow space for expired air. The prior interface pillows style interface does not let the patient feel as if their expiratory cycle is normal. This is perceived as an increase in work of breathing. Adequate cross-sectional flow space for exhaled air can only be provided if there is an adequate volume of air supplied to the inspiratory cycle with very little or no resistance accompanied with a low air velocity which simulates normal inspiratory/expiratory flow rate.

The expiratory cycle is normally completed during deep sleep and is achieved only by the elasticity of the patient's lung. Accessory muscles are not active during restful sleep. If inspired air is not normally exhaled the patient will not feel secure and deep sleep will not come easy. The inspired air is not being normally exhaled if the patient's respiratory rate has been disrupted.

Further, bleed ports in prior systems direct exhaled air flow onto the patient's arms/hands. Some bleed ports are embodied into a swivel adaptor that can unintentionally misdirect exhale air flow in an unwanted direction. Constant adjustment is often needed. The patient's breathing mechanics must function as if they are not using CPAP therapy, and the CPAP therapy must correct apneic events to promote a sound, prolonged sleep, and consistent compliance to treatment. For the vast majority of patients using prior interface pillows, this requires a high volume of air delivery; significantly lower air velocity; and using significantly less pressure.

It is desired that the patient experiences no change in noise of air flow throughout the inspiratory/expiratory cycle. Any change in air flow noise during any part of the ventilation cycle indicates the patient's normal breathing is being interrupted. This is typically caused by an inadequate volume of inspired air and inadequate flow space for exhaled air. When a high volume of air is provided then a low level of pressure is required to correct apneic events for the vast majority of patients. Apneic events are not sudden; they build. If an ample/adequate volume of inspired air is supplied with a lower pressure, apneic events are prevented. If adequate inspired air volume is not available, then apneic events eventually occur during sleep and pressure will need to be increased to compensate for inadequate volume. To this end, sleep technicians often increase driving pressures as the sleep cycles progress. The increase in driving pressure is not preferred over adequate volume, often only partially compensates for an air volume deficiency, and typically increases unwanted effects.

Another issue with existing continuous positive air pressure systems is disposal of extra pressure, either from the air flow generator or from the user's exhalation. Many existing continuous positive air pressure systems have inadequate exit venting or exit venting that is directed toward the user's body, creating discomfort as the user exhales.

What is needed is a continuous positive air pressure system that provides interface pillows that seal against the edge of the nostrils while retaining comfort and proper air flow.

SUMMARY

In one embodiment, an integrated cannula with interface pillows is disclosed. The interface pillows are for sealing with a nostril of a user. The integrated cannula with interface pillows includes a cannula section having a gas inlet for receiving the gas from a source of gas, exhalation holes for venting exhalation gas to the atmosphere, and nubs for attaching a head strap. There are two interface pillows formed from a pliable material extend from the cannula section. Each of the interface pillows having an insertion tip that is distal from where each of the interface pillows meets the cannula section. An insertion bulge extends from each interface pillow between the insertion tip and the cannula section, limiting an insertion distance of the insertion tip. An insertion area of each interface pillow extends between the insertion bulge and the insertion tip during use, the insertion bulge is configured to seal against an outer edge of the nostril of a nose.

In another embodiment, integrated cannula with interface pillows is disclosed. The interface pillows seal against a nostril of a nose of user. The integrated cannula with interface pillows includes a cannula section that has a gas inlet for receiving the gas from a source of gas, exhalation holes for venting exhalation gas to the atmosphere, and nubs for attaching a head strap. There are two interface pillows formed with the cannula section and made of a pliable material. Each of the interface pillows has an insertion tip distal from the cannula section and an insertion bulge for limiting an insertion distance of the insertion tip to approximately 0.25 inches. An insertion area of each of the interface pillows extends between the insertion tip and the insertion bulge, sides of which taper inwardly towards the insertion tip at an angle, thereby a cross-sectional area of the insertion tip is smaller than a second cross-sectional area at a point where the insertion area meets the insertion bulge. The insertion bulge of each of the interface pillows seals against an outer edge of the nostril of the nose.

In another embodiment, a method of delivering positive airway pressure to the user is disclosed using the integrated cannula with interface pillows described above. The method includes inserting the insertion area of each of the two interface pillows into respective nostrils of the user until the insertion bulge of each of the two interface pillows interfaces with an outer edge of the respective nostrils of the user. The insertion area of each of the two interface pillows extending into the respective nostril of the user and the insertion bulge of each of the two interface pillows deform under pressure from the cannula section and seal against the edge of the respective nostrils of the user. Gas from the cannula section flow through the two interface pillows and into the user's nostrils.

In another embodiment, an interface pillow for insertion into a nostril of a user is disclosed. The interface pillow includes a body made of a pliable material. The body has an insertion tip and a connection interface that is distal from the insertion tip. The connection interface is for interfacing with a cannula. An insertion bulge extends from the body between the insertion tip and the connection interface. The insertion bulge limits an insertion distance of the insertion tip. An insertion area of the body extends between the insertion bulge and the insertion tip so that, when in use, the insertion bulge is configured to seal against an outer edge of the nostril of a nose.

In another embodiment, an interface pillow for insertion into a nostril of a user is disclosed. The interface pillow includes a body made of a pliable material. The body has an insertion tip and a connection interface that is distal from the insertion tip. The connection interface is for interfacing with a cannula. The body includes an insertion bulge that extends from the body for limiting an insertion distance of the insertion tip to approximately 0.25 inches. An insertion area of the body extends between the insertion tip and the insertion bulge. Sides of the insertion area taper inwardly towards the insertion tip at an angle, thereby a cross-sectional area of the insertion tip being smaller than a second cross-sectional area at a point where the insertion area interfaces to the insertion bulge. When in use, the insertion bulge is configured to seal against an outer edge of the nostril of a nose.

In another embodiment, a method of delivering positive airway pressure to the user using the above-described interface pillows is disclosed. The method includes connecting two interface pillows to the cannula that is interface to a source of air flow and inserting the insertion area of each of the two interface pillows into respective nostrils of the user until the insertion bulge of each of the two interface pillows interfaces with an outer edge of the respective nostrils of the user. After insertion, the insertion area of each of the two interface pillows extends into the respective nostril of the user (e.g., by 0.25 inches). After insertion, the insertion bulge of each of the two interface pillows deforms under pressure from the cannula and seals against the edge of the respective nostrils of the user so that air from the cannula flows through the two interface pillows and into the user's nostrils without leaking.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
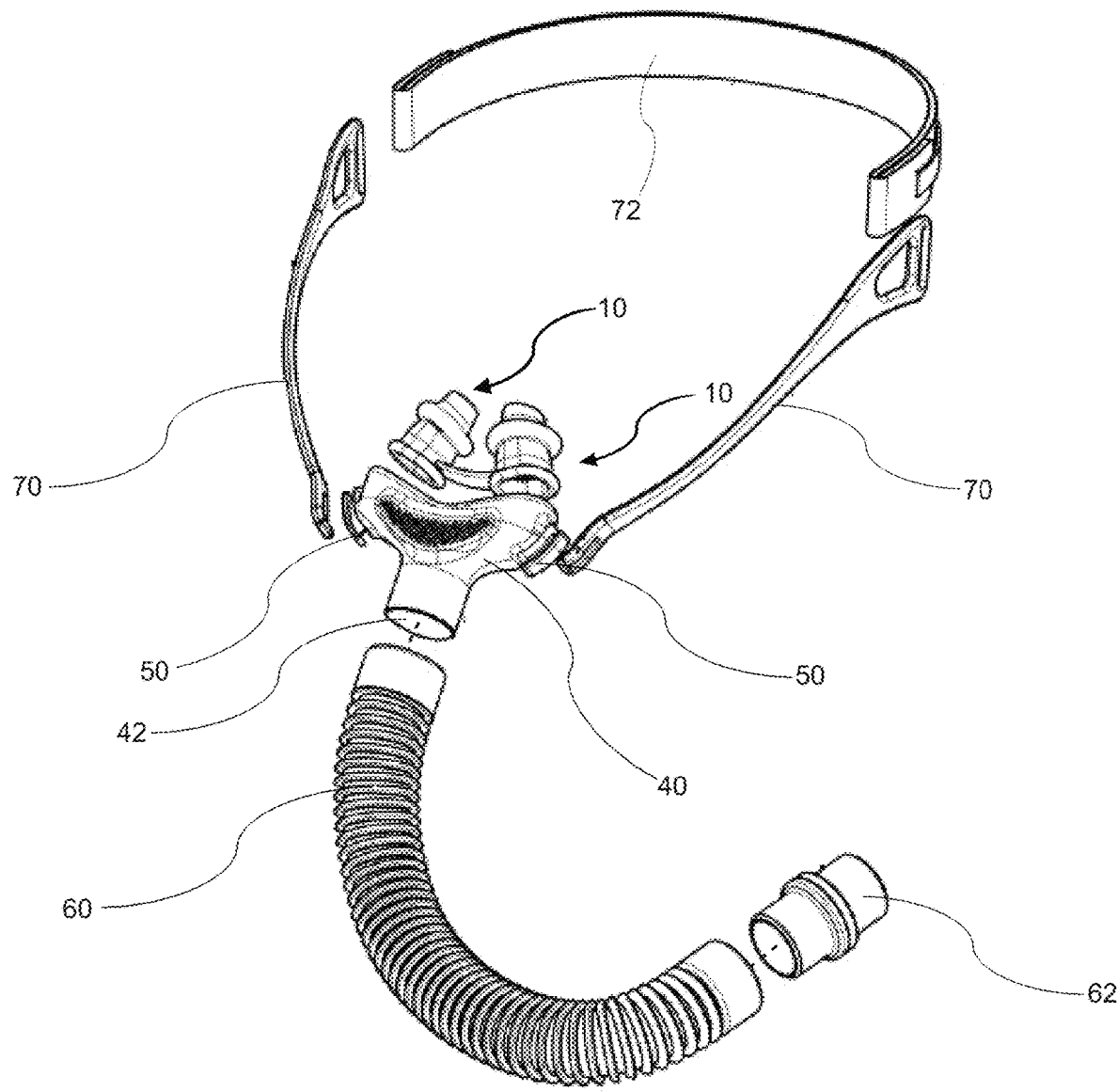
FIG. 1 illustrates a perspective view of a system of the present invention.

Reference will now be made in detail to the presently preferred embodiments of the invention, examples of which are illustrated in the accompanying drawings. Throughout the following detailed description, the same reference numerals refer to the same elements in all figures.

The present invention provides an adequate air volume, allowing for a normal inspiratory cycle and allowing normal adequate exhalation while treating, for example, sleep apneas. The high volume delivery is provided at decreases air flow velocity, increasing lateral pressure, decreasing of the venturi effect, and increasing the effectiveness of treatment. The present invention is designed so as to not interrupt a patient's normal breathing mechanics; therefore, not interrupting a patient's normal respiratory rate and not interrupting a patient's normal inspiratory/expiratory ratio.

Work of breathing is greatly diminished. There is reduced turbulence or restriction during the inspiratory cycle with little or no noticeable change in noise throughout the inspiratory/expiratory cycle. The patient is able to exhale completely via the patient's elasticity of the lungs and without the use of any accessory muscles. Respiratory rate typically remains normal at 12 to 14 breaths per minute. The patient maintains normal minute ventilation throughout the night. Heart rate and oxygen saturation remain optimal throughout the night. The patient experiences normal breathing without apneic events. Once initial pressures are set during polysomnography, there is no need for increasing pressures at any time throughout the sleep cycle. These benefits result into a significant increase in compliance to the treatment (e.g., the patient continues to use the system).

Throughout this description, the continuous positive air pressure system is described in relationship to being used by a user, wearer, patient, etc., interchangeably. There is no limitation as to who will used the continuous positive air pressure system described here within.

Referring to FIG. 1, a perspective view of a system of the present invention is shown. The system shown in FIG. 1 is a continuous positive air pressure system that receives air flow from a source (not shown), connected to flexible tube 60 at one end by a swivel adapter 62. Current systems typically provide air flow to the flexible tube 60, which is often a 22 millimeter flexible tube 60. The present application requires a source of air flow, but is in no way limited to any particular source of a gas (e.g. air, concentrated air, oxygen, etc.) and is not limited in any way to specific plumbing for delivery of such air flow.

A distal end of the flexible tube 60 connects to an air supply port 42 of the cannula 40. In general, the cannula is substantially hollow. As the continuous positive air pressure system is typically worn while sleeping, the continuous positive air pressure system need be retained to the person using the continuous positive air pressure system.

Although there is no limitation as to how the continuous positive air pressure system is held to the user, in the embodiment shown, the cannula 40 includes tabs 50 for attaching a retainer 70/72. In some embodiments, the retainer 70/72 includes an adjustable portion 72 for conforming to a head size of a wearer (e.g. having hook/loop material adjustments) and resilient members 70 that provide some amount of tension, holding the cannula 40 in place, and therefore, retaining the interface pillows 10 within the wearer's nostrils. For example, in some embodiments the resilient members 70 are made from medical grade silicone. The interface pillows 10 are describe in detail along with FIGS. 2 and 3.

Note that interface pillows of the prior art are typically made of a very soft and pliable material and have an overall round cross-sectional shape. When such is inserted into the nostril of a wearer, the round shape must conform to an internal shape of the user's nostrils, leading to both discomfort and impacted air passages that result in higher velocity of air flow and noise.

Figure 2:
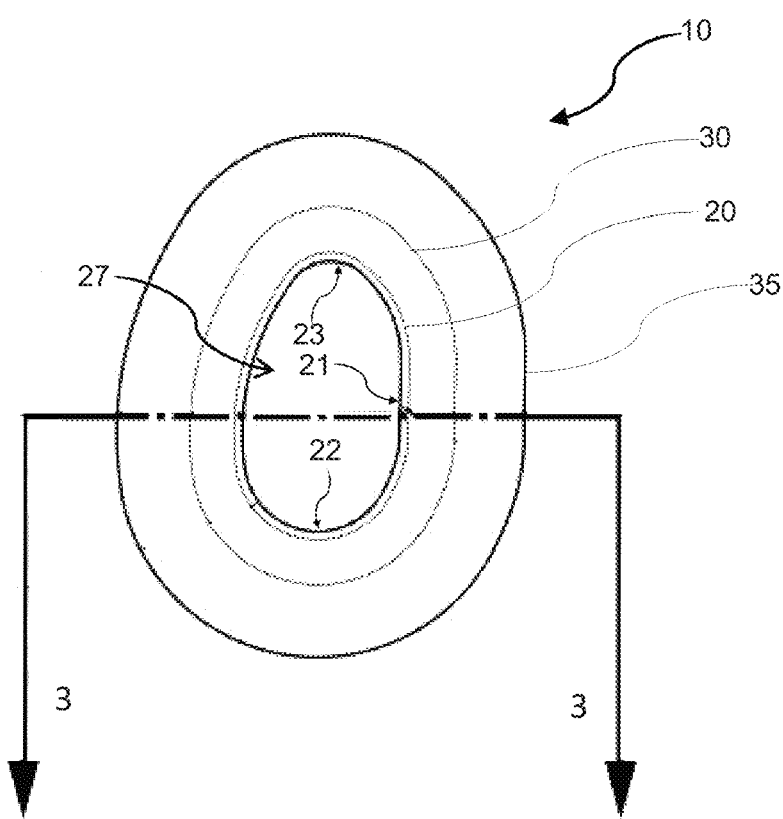
FIG. 2 illustrates a bottom plan view of a pillow interface of the present invention.
Figure 3:
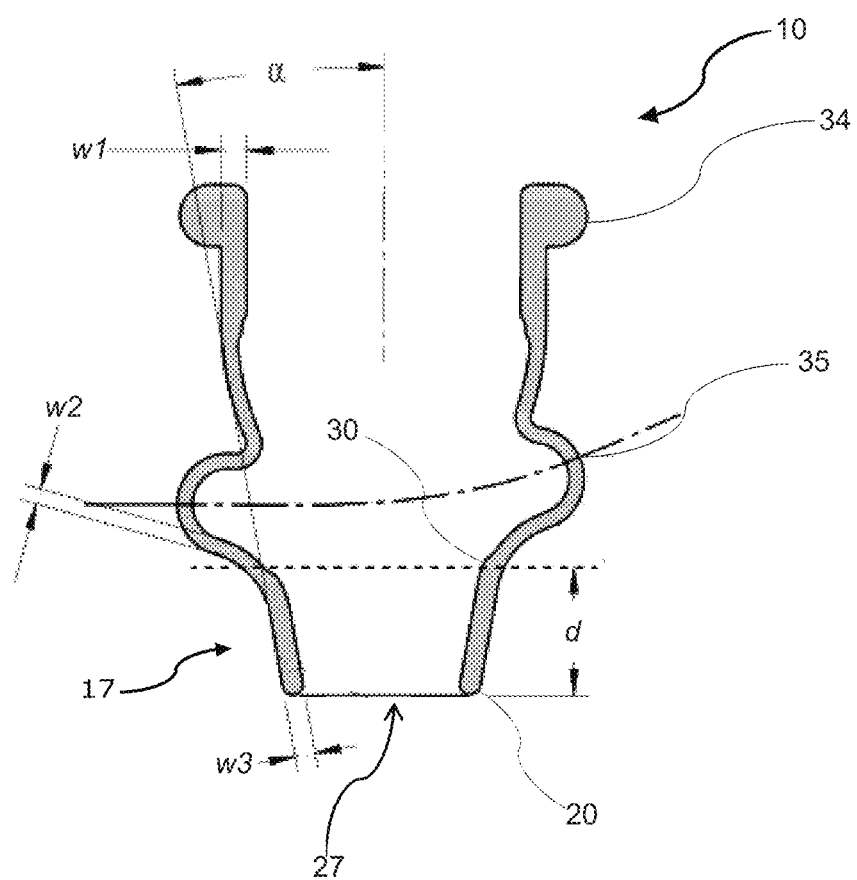
FIG. 3 illustrates a cross-sectional view of the pillow interface of FIG. 2 along lines 3-3.

Referring to FIGS. 2 and 3 a bottom plan view and a cross-sectional view of the interface pillows 10 is shown. The interface pillows 10 fit into and against the outer portion (entry area) of the wearer's nostrils. In general, the interface pillows 10 are made as pliable members (e.g. deform slightly under pressure) having a body that is elongated with one end for interfacing with a cannula 40 and a distal end for insertion partially into a wearer's nostril.

Viewing one interface pillow 10 from the bottom (FIG. 2), the insertion depth, d, is defined by a side that slopes outwardly from the insertion tip 20 to a point of insertion 30. The insertion slope is an angle, a, that in some embodiments is 10 degrees from a center axis of the interface pillow 10. Proper insertion is limited by an insertion bulge 35 that prevents over-insertion of the interface pillows 10 into the nostrils of the wearer an provides a seal at seal points 51/52 (see FIG. 7) against the edge of the wearer's nostril 80 and septum 82 (see FIG. 7). Each interface pillow 10 has a connection interface 34 (canula end) for connecting to the cannula 40 (see FIGS. 4-6). In some embodiments, the insertion depth if the insertion area 17, d, is set at approximately 0.25" for a comfortable depth extending inside the patient's nostril, e.g., an insertion distance of d.

The cross-sectional shape of the interface pillow 10 is formed to provide an enhanced seal of the insertion bulge 35 against the edges of the wearer's nostril 80 and septum 82 while providing maximum comfort. Note that the view from the bottom shown in FIG. 2 is that of an interface pillow 10 that is to be worn in the left nostril, as the interface pillow 10 that is to be worn in the right nostril is flipped to match the symmetry of the wearer's nose.

The cross-sectional shape of the interface pillow 10 is shown having three specific nose interface areas 21/22/23. The septum of the wearer's nose is generally flat and relatively unyielding. The septum interface area 21 has a flattened side to rest comfortably against the wearer's septum when inserted (e.g., into the left nostril). The upper interface area 23 is rounded and narrow with respect to the lower interface area 22, as the geometry/shape of most nostrils are wider towards the mouth of the wearer than they are towards the brow of the wearer. In this, the interface area 22 next to the insertion bulge is the widest, dilating the lower region of the wearer's nostril the most, as the lower region of the wearer's nostril is also the least sensitive.

This shape of the insertion area 17 provides both a good seal and improved comfort. The shape of the insertion area 17 enables the interface pillows 10 to be made of a stiffer or thicker material than those of the prior art as there is no need for the insertion area 17 to deform. In such, upon insertion into the nostrils, the insertion area 17 of the interface pillows 10 generally retain their shape and, therefore, do not restrict air flow through the air channel 27. Further, testing has shown that the shape of the insertion area 17 and insertion bulge 35 of the interface pillows 10 maintains the seal as seal points 51/52 even at the highest pressures expected with existing air pressure sources, typically around 20 centimeters of water pressure.

The insertion area of the cushion which fits against the inside of the nostrils 80/82 is at an angle, a, that in some embodiments is 10 degrees from a center axis of the interface pillow 10. When the interface pillow 10 is pressed against the nostrils, the septum 82 of the nostril remains steadfast while the outside of the nostril 80 are flexible and gives way slightly, for example, 0.10 inch.

In FIG. 3, a cross section of one interface pillow 10 is shown. This illustrates shows that the insertion area 17 of the interface pillow 10 is angled at an angle of a to reduce pressure from being exerted against the septum. The insertion tip 20 is preferably rounded. Generally, the outside area of the nostril 80 will give way by, for example, 0.10 inches, while the septum 82 remains stationery. The angle of the insertion area 17 compensates for the uneven distribution of pressure against the bottom of the nostrils 80/82 while in use. The result is significantly greater comfort, and much greater seal capacity with much less chance of an air leak resulting in lesser efficiency and increased noise.

In some embodiments, the wall thicknesses vary. In some such embodiments, at the insertion area 17, the insertion wall thickness w3 is 0.04 inches and narrows to a wall thickness w2 of 0.03 inches at the insertion bulge 35. These dimensions promote a forgiving feel of the pillows cushion against the bottom edge of the nostril, while maintaining an open air channel 27 at the insertion area 17 when inserted into the nostrils. At the connection interface 34, the thickness, w1, is, for example, 0.05 inches. Note that in embodiments in which the insertion bulge 35 is made of a thinner, more flexible material (wall thickness w2) than the insertion area 17 (insertion wall thickness w3), the insertion bulge 35 is more flexible and deforms under sealing pressure from the cannula 40 whereas the insertion area 17 is firmer and deforms less, thereby not significantly deforming within the user's nostril and, therefore, not causing turbulence and/or flapping as air flows in/out of the air channel 27. Note that in some embodiments, the geometry of insertion bulge 35 is such that the insertion bulge 35 is closer to the insertion tip 20 at one side of the interface pillow 10 than at the distal side of the interface pillow 10, compensating for the septum 82 extending further from the nose than the outer edges of the nostril 80 (see FIG. 7).

Figure 4:
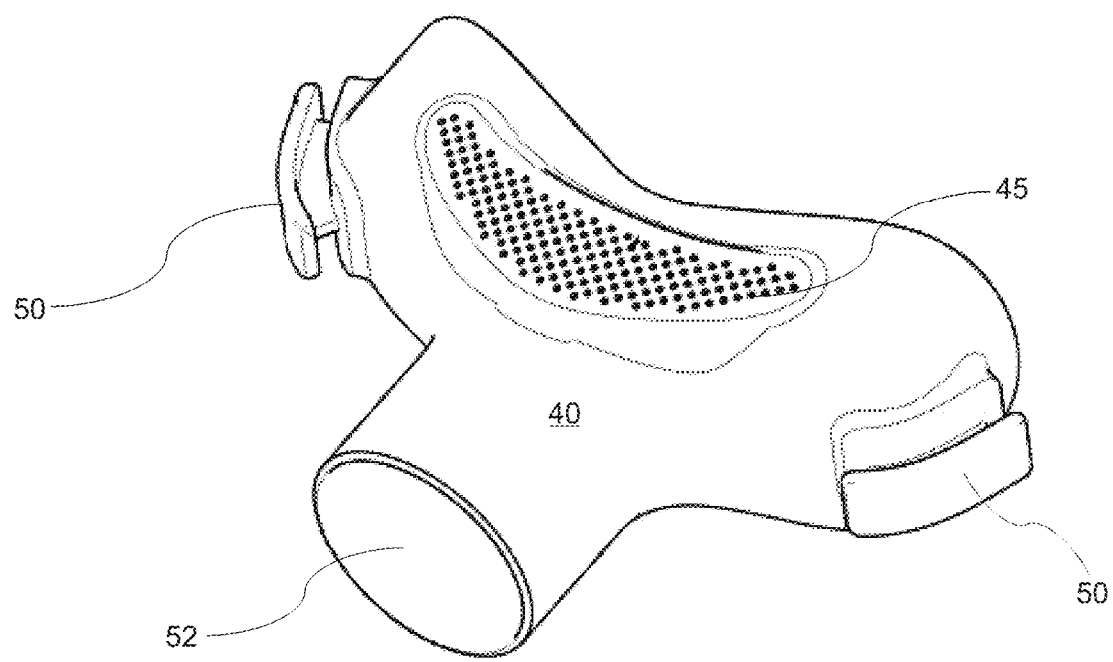
FIG. 4 illustrates a perspective view of the cannula of the present invention.
Figure 5:
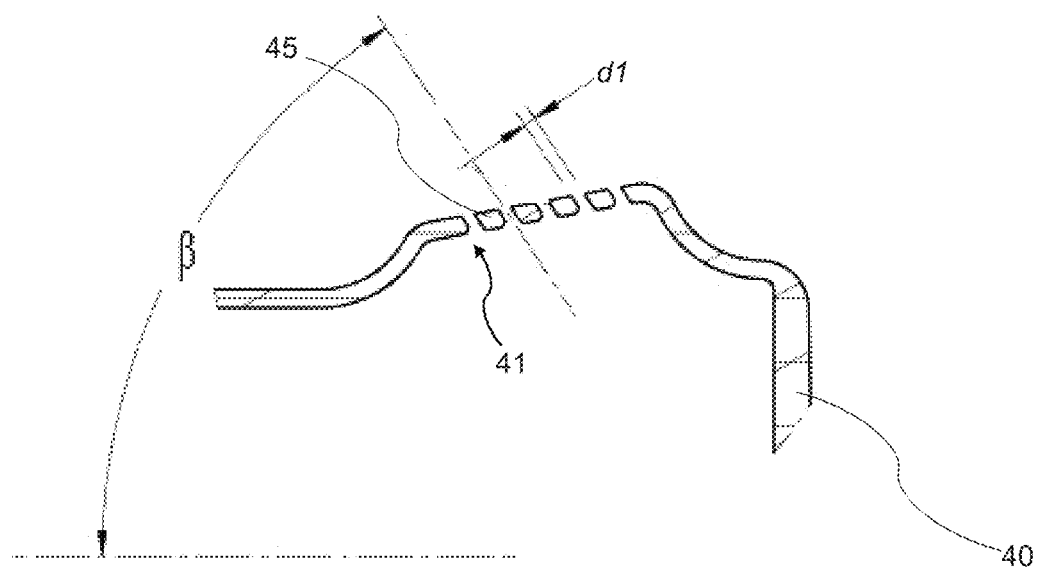
FIG. 5 illustrates a cut-away partial view of the cannula of the present invention.
Figure 6:
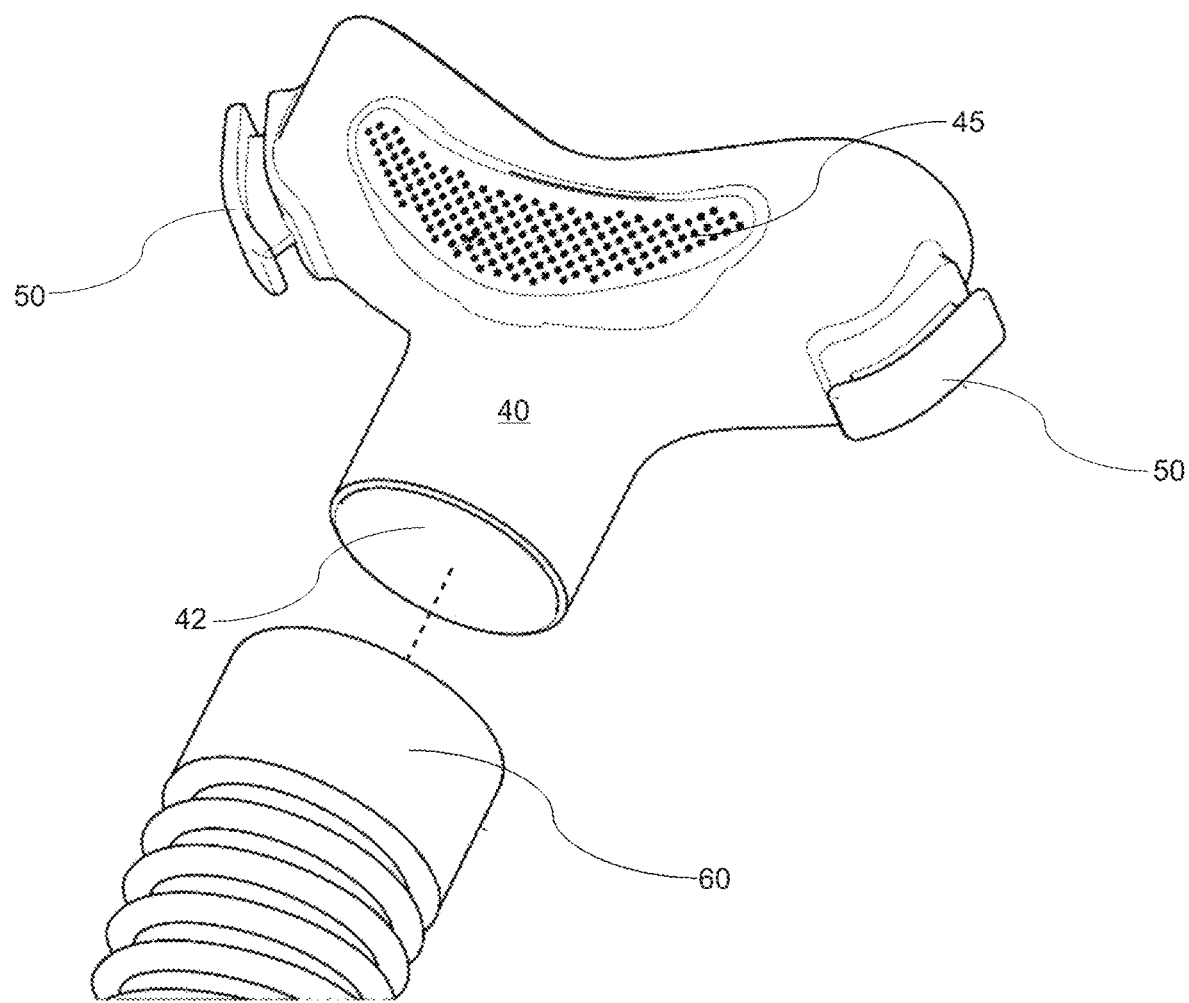
FIG. 6 illustrates a perspective view of the cannula of the present invention being connected to a source of air flow.

Referring to FIGS. 4 through 6, perspective views of the cannula 40 of the present invention are shown. The cannula 40 is preferably hollow. The bleed port section 45 of the cannula 40 allows the user to exhale. The bleed port section 45 is placed in the front of the cannula body and directs exhalation air flow in a direction away from the arms/hands of a wearer, especially when the wearer is sleeping on their side. The exhaled air flow is directed at an angle, β which is, for example, 57 degrees with respect to a lengthwise axis of the cannula 40. The bleed port section 45 is composed of bleed holes 41, each having an internal diameter, for example an internal diameter of 0.02". In some embodiments, there are approximately 160 bleed holes 41. This provides a 0.05" square inch cross-sectional flow space per bleed hole 41 which is equivalent to a 0.25" diameter bleed hole. This flow space for exhaled air is much greater than that of the prior art. This flow space eliminates, or greatly reduces, work of breathing. This volume of flow space for exhaled air is possible because of the high volume of incoming air made available through the open flow space within the interface pillows 10.

Figure 7:
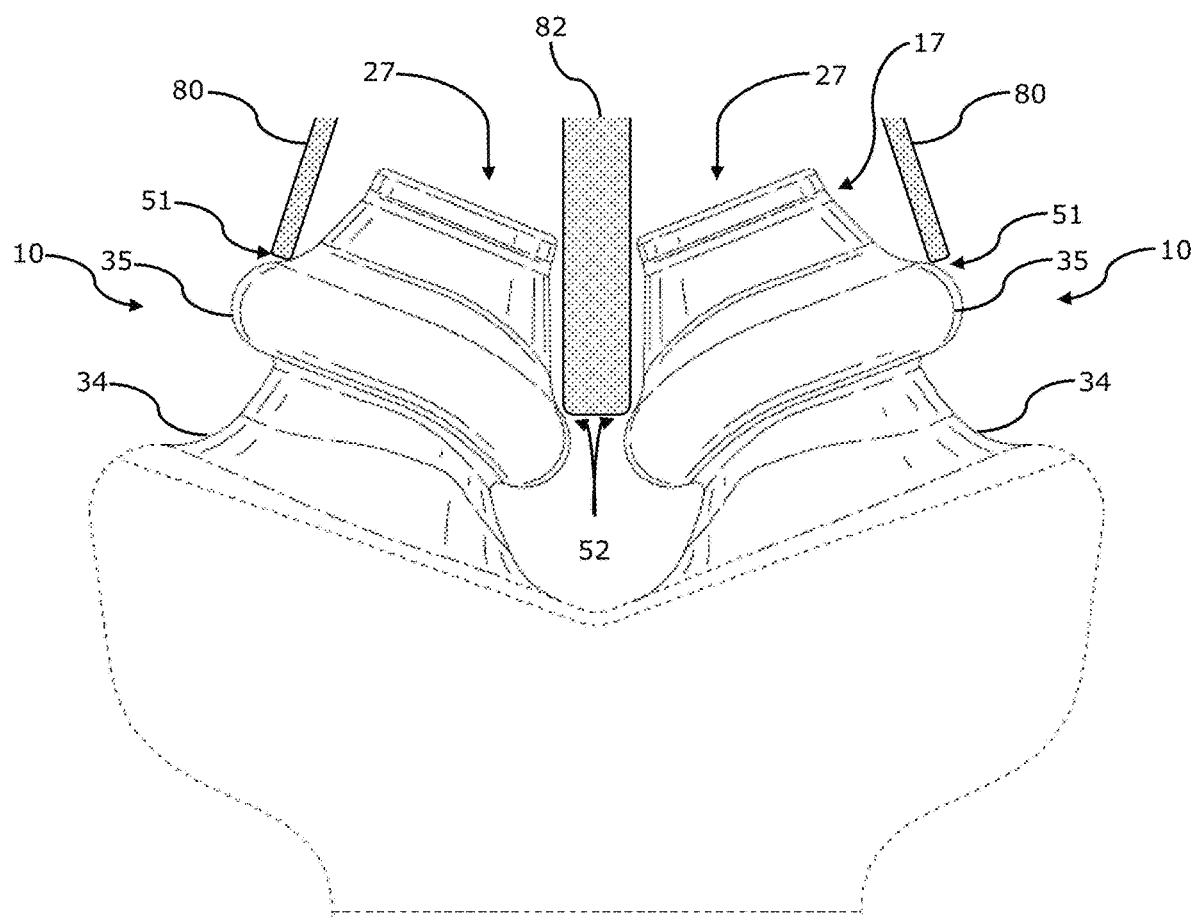
FIG. 7 illustrates a pillow interface of the present invention abutting against the edge of a nostril.

Referring to FIG. 7, an interface pillow 10 of the present invention is shown attached to a canula and abutting against the edge of a nostril 80/82. In FIG. 7, it is shown that the edges of the nostril 80/82 contact the insertion bulge 35, where the insertion bulge 35 seals against the edges of the nostril 80/28. The insertion bulge 35 seals against the outer edges of the nostril 80 at seal points 51 and the insertion bulge 35 seals against the septum 82 at seal points 52. It is also shown, as in the geometry of most noses, that the septum 82 is not even with the outer edges of the nostril 80. Therefore, the insertion bulge 35 is curved slightly downward towards the septum 82 to exert substantially similar pressure against the septum 82 as against the outer edges of the nostril 80.

Figure 8:
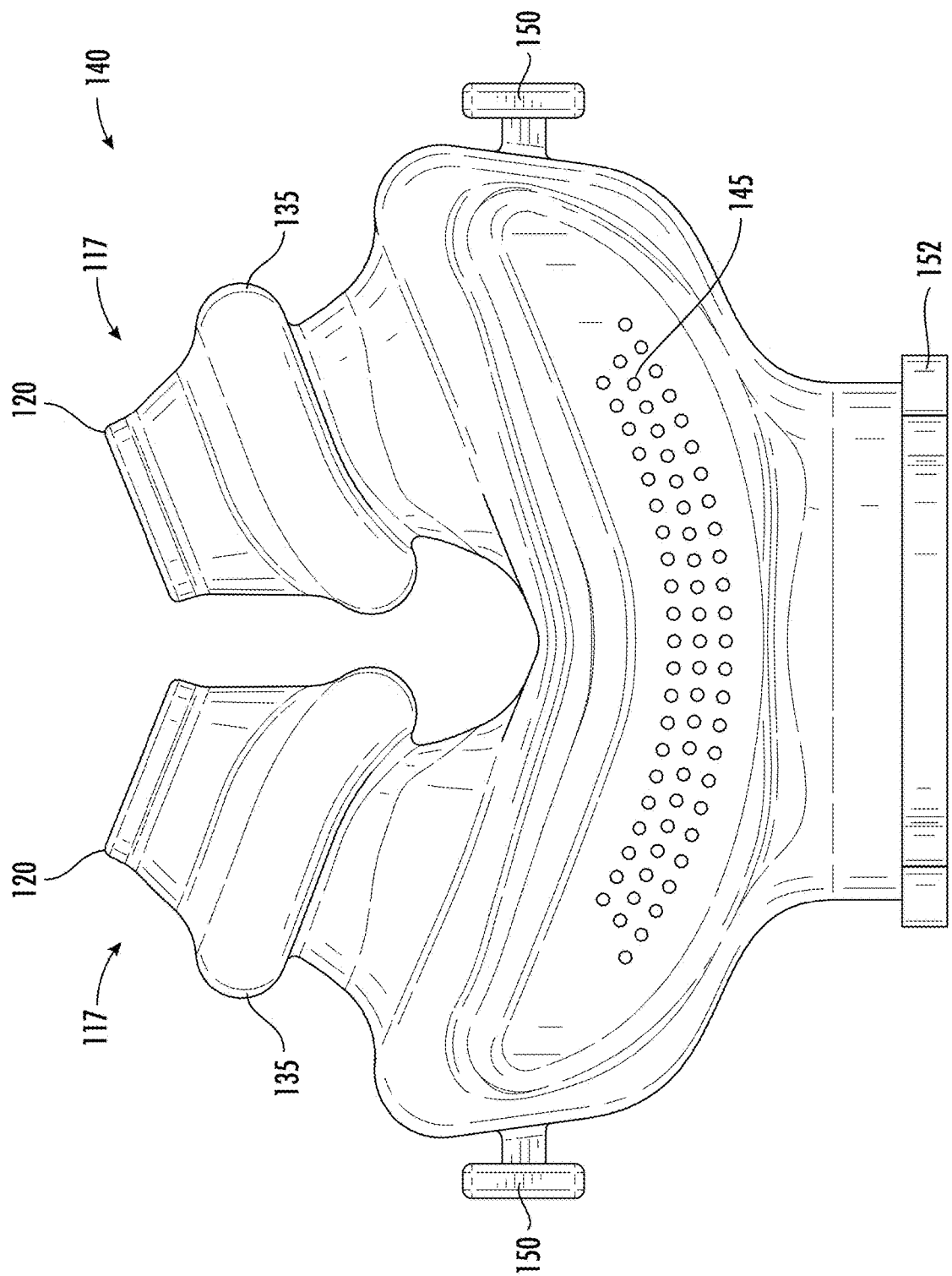
FIG. 8 illustrates a cannula with pillow interface of the present invention.

Referring to FIG. 8, a cannula with integrated pillow interface 140 of the present invention is shown. In this embodiment, the cannula 40 (cannula section) and pillows 10 are integrated/formed/molded into an integrated cannula with integrated pillow interface 140. In this, the pillows interface is similar to or the same as the pillow 10 described above. The integrated insertion tip 120, the integrated insertion area 117, and integrated insertion bulge 135 are the same as the insertion tip 20, the insertion area 17, and insertion bulge 35 described with the pillow 10 above, only instead of having a connection interface 34, the integrated pillow is formed as part of the cannula 40 into the cannula with integrated pillow interface 140. The cannula with integrated pillow interface 140 includes several exhalation holes 145 (or bleed holes) for exhausting of exhalation gases from the user. Note that in some embodiments, the exhalation holes 145 are formed at an angle and aimed away from the user so that exhalation gases flow outwardly and away from the user instead of directly at the user. There are nubs 150 for connecting to a head strap 160 (see FIG. 9), the head strap holding the cannula with integrated pillow interface 140 against the user's nose as will be described with FIG. 9.

In some embodiments, the air delivery connector 152 snap-connects to the air delivery tube 60, forming a swivel connection and allowing for rotating of the air delivery tube 60 for proper positioning.

Figure 9:
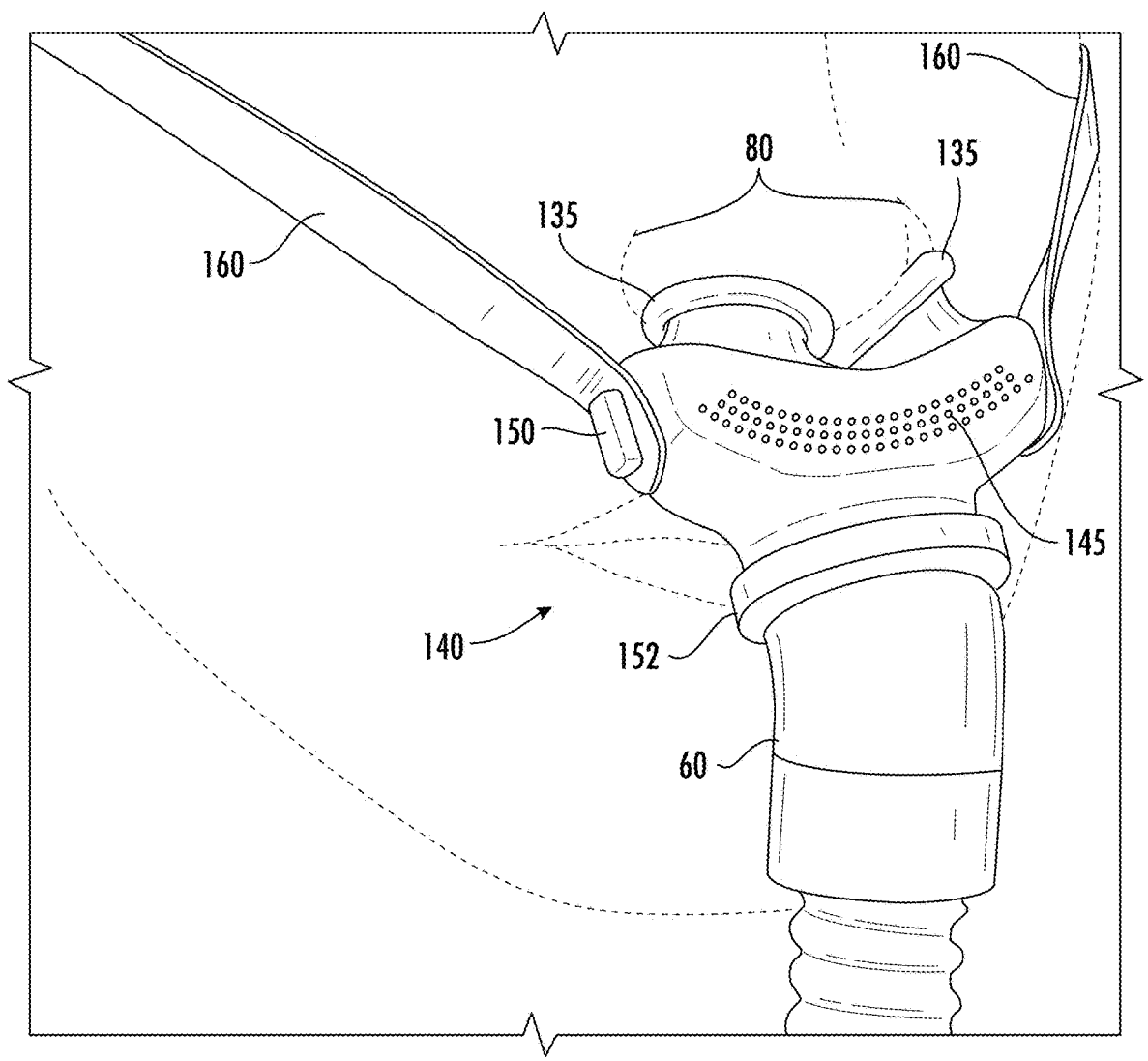
FIG. 9 illustrates a cannula with pillow interface of the present invention abutting against the edge of a nostril.

FIG. 9 illustrates the cannula with integrated pillow interface 140 of the present invention abutting against the edge of a nose 80. In this view, the integrated insertion bulge 135 is shown abutting the edge of the user's nose 80, forming a seal against the edge of the user's nose 80 (note a portion of the user's head and nose 80 are shown in dashed lines). In this view, the integrated insertion tip 120 and the integrated insertion area 117 are within the user's nose 80 and, therefore, not visible.

The nubs 150 are shown connected to a head strap 160 and the head strap holds the cannula with integrated pillow interface 140 against the user's nose 80, forming the seal between the user's nose 80 and the integrated insertion bulge 135.

In the embodiment shown, the air delivery connector 152 snap-connects to the air delivery tube 60, forming a swivel connection, allowing for rotating of the air delivery tube 60 for proper positioning.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An integrated cannula with interface pillows, the interface pillows for sealing with a nostril of a user, the integrated cannula with interface pillows:
    a cannula section having a gas inlet for receiving a gas from a source of gas, exhalation holes for venting exhalation gas to atmosphere, and nubs for attaching a head strap;
    two interface pillows formed from a pliable material extend from the cannula section, each of the interface pillows has an insertion tip that is distal from where each of the interface pillows meets the cannula section;
    an insertion bulge extending from each interface pillow between the insertion tip and the cannula section, the insertion bulge limits an insertion distance of the insertion tip;
    an insertion area of each interface pillow extends between the insertion bulge and the insertion tip, the insertion area having sides that angle inwardly towards the insertion tip at an angle, thereby a cross-sectional area of the insertion tip being smaller than a second cross-sectional area at a point where the insertion area interfaces to the insertion bulge, an outer shape of the insertion area is planar on one side for interfacing with a septum of a nose; and
    whereas when in use, the insertion bulge is configured to seal against an outer edge of the nostril of a nose;
    wherein the exhalation holes are formed at an angle with respect a surface of the cannula on which the exhalation holes are formed, thereby exhalation gases are aimed outwardly for venting the exhalation gas in a direction away from the two interface pillows.

2. The integrated cannula with interface pillows of claim 1, wherein sides of the insertion area diverge at an angle of 10 degrees between the insertion bulge and the insertion tip.

3. The integrated cannula with interface pillows of claim 1, wherein a first thickness of each of the interface pillows at the insertion area is greater than a second thickness of each of the interface pillows at the insertion bulge.

4. The integrated cannula with interface pillows of claim 3, wherein the first thickness of each of the interface pillows at the insertion area is 0.04 inches and the second thickness of each of the interface pillows at the insertion bulge is 0.03 inches.

5. The integrated cannula with interface pillows of claim 1, wherein a distance from the insertion bulge to the insertion tip is 0.25 inches.

6. A method of delivering positive airway pressure to the user using the integrated cannula with interface pillows of claim 1, the method comprising:

inserting the insertion area of each of the two interface pillows into respective nostrils of the user until the insertion bulge of each of the two interface pillows interfaces with an outer edge of the respective nostrils of the user, the insertion area of each of the two interface pillows extending into the respective nostril of the user and a planar area on one side of each the interface pillows interfaces with a septum of a respective nostril;

the insertion bulge of each of the two interface pillows deforming under pressure from the cannula section and sealing against the edge of the respective nostrils of the user; and the gas from the cannula section flowing through the two interface pillows and into the nostrils of the user.

7. The method of claim 6, wherein the insertion area of each of the two interface pillows extending into each of the nostrils of the user by an insertion depth of 0.25 inches.

8. The method of claim 6, wherein sides of the insertion area of each of the interface pillows diverging at an angle of 10 degrees between the insertion bulge and the insertion tip.

9. The method of claim 6, wherein a first thickness of each of the interface pillows at the insertion area is greater than a second thickness of each of the interface pillows at the insertion bulge.

10. The method of claim 9, wherein the first thickness of each of the interface pillows at the insertion area is 0.04 inches and the second thickness of each of the interface pillows at the insertion bulge is 0.03 inches.

11. An integrated cannula with interface pillows, the interface pillows for sealing against a nostril of a nose of a user, the integrated cannula with interface pillows comprising:

a cannula section that has a gas inlet for receiving a gas from a source of the gas, exhalation holes for venting exhalation gas to atmosphere, and nubs for attaching a head strap;

two interface pillows formed with the cannula section and made of a pliable material, each of the interface pillows has an insertion tip distal from the cannula section;

each of the interface pillows includes an insertion bulge for limiting an insertion distance of the insertion tip to approximately 0.25 inches;

an insertion area of each of the interface pillows extends between the insertion tip and the insertion bulge, sides of the insertion area tapers inwardly towards the insertion tip at an angle, thereby a cross-sectional area of the insertion tip is smaller than a second cross-sectional area at a point where the insertion area meets the insertion bulge, an outer shape of the insertion area is planar on one side for interfacing with a septum of a nose; and the insertion bulge of each of the interface pillows seal against an outer edge of the nostril of the nose.

12. The integrated cannula with interface pillows of claim 11, wherein the angle is 10 degrees.

13. The integrated cannula with interface pillows of claim 11, wherein a first thickness of each of the interface pillows at the insertion area is greater than a second thickness of each of the interface pillows at the insertion bulge.

14. The integrated cannula with interface pillows of claim 13, wherein the first thickness of the insertion area is 0.05 inches and the second thickness of each of the interface pillows at the insertion bulge is 0.03 inches.

15. The integrated cannula with interface pillows of claim 11, wherein the exhalation holes are on an upper surface of the cannula section and the exhalation holes aim away from an end at which the interface pillows meet the cannula section, thereby the exhalation holes direct the exhalation gas away from the user.

* * * * *